US00PP22022P2

(12) United States Plant Patent
Heuger

(10) Patent No.: US PP22,022 P2
(45) Date of Patent: Jul. 5, 2011

(54) ***HELLEBORUS* PLANT NAMED 'COSEH 740'**

(50) Latin Name: *Helleborus×ericsmithii*
Varietal Denomination: COSEH 740

(76) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 12/798,346

(22) Filed: Mar. 31, 2010

(51) Int. Cl.
*A01H 5/00* (2006.01)

(52) U.S. Cl. ..... Plt./439
(58) Field of Classification Search ..... Plt./439
See application file for complete search history.

*Primary Examiner* — Annette H Para
(74) *Attorney, Agent, or Firm* — C. A. Whealy

(57) ABSTRACT

A new and distinct cultivar of *Helleborus* plant named 'COSEH 740', characterized by its upright and outwardly arching plant habit; uniform flowering habit; dark green-colored leaves; long flowering period; numerous single white-colored flowers; and good garden performance.

2 Drawing Sheets

Botanical designation: *Helleborus×ericsmithii.*
Cultivar denomination: 'COSEH 740'.

BACKGROUND OF THE INVENTION

The present invention relates to a new and distinct cultivar of *Helleborus* plant, botanically known as *Helleborus×ericsmithii*, and hereinafter referred to by the name 'COSEH 740'.

The new *Helleborus* plant is a product of a planned breeding program in Glandorf, Germany. The objective of the breeding program was to create new uniform *Helleborus* cultivars with unique and attractive flower coloration and resistance to pests.

The new *Helleborus* plant originated from a cross-pollination conducted by the Inventor in Glandorf, Germany in November, 2002 of two unnamed proprietary seedling selections of *Helleborus×ericsmithii*, not patented. The new *Helleborus* plant was discovered and selected by the Inventor as a single flowering plant from within the progeny of the stated cross-pollination grown in a controlled greenhouse environment in Glandorf, Germany in February, 2005.

Asexual reproduction of the new *Helleborus* plant by divisions in a controlled greenhouse environment in Glandorf, Germany since March, 2005, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'COSEH 740'. These characteristics in combination distinguish 'COSEH 740' as a new and distinct cultivar of *Helleborus* plant:

1. Upright and outwardly arching plant habit.
2. Uniform flowering habit.
3. Dark green-colored leaves.
4. Long flowering period.

5. Numerous single white-colored flowers.
6. Good garden performance.

Compared to plants of the parent selections, plants of the new *Helleborus* flower more freely and more uniformly.

Plants of the new *Helleborus* can be compared to plants of *Helleborus niger×Helleborus lividus* 'COSEH 710', disclosed in U.S. Plant patent application Ser. No. 12/319,424. Plants of the new *Helleborus* differ primarily from plants of 'COSEH 710' in the following characteristics:

1. Plants of the new *Helleborus* are not as vigorous as plants of 'COSEH 710'.
2. Flowers of plants of the new *Helleborus* are white in color whereas flowers of plants of 'COSEH 710' are light green in color with reddish pink overtones.

BRIEF DESCRIPTION OF THE PHOTOGRAPHS

The accompanying colored photographs illustrate the overall appearance of the new *Helleborus* plant, showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 740' grown in a container.

The photograph on the second sheet is a close-up view of a typical flower of 'COSEH 740'.

DETAILED BOTANICAL DESCRIPTION

The aforementioned photographs and following observations, measurements and values describe plants grown in Glandorf, Germany in 1.5-liter containers during the winter in a glass-covered greenhouse and under conditions which closely approximate commercial *Helleborus* production. During the production of the plants, day temperatures ranged from 12° C. to 32° C. and night temperatures ranged from 3° C. to 18° C. Plants were one year old when the photographs and the description were taken. In the following description, color references are made to The Royal Horticultural Society Colour Chart, 2007 Edition, except where general terms of ordinary dictionary significance are used.

Botanical classification: *Helleborus×ericsmithii* 'COSEH 740'.

Parentage:

*Female, or seed, parent.*—Unnamed proprietary seedling selection of *Helleborus×ericsmithii*, not patented.

*Male, or pollen, parent.*—Unnamed proprietary seedling selection of *Helleborus×ericsmithii*, not patented.

Propagation:

*Type.*—By tissue culture.

*Time to initiate roots.*—About two months at 12° C.

*Time to produce a rooted young plant.*—About six months at 4° C. to 15° C.

*Root description.*—Thick to thin, fleshy; white to brown in color.

*Rooting habit.*—Sparse.

Plant description:

*Plant form and growth habit.*—Herbaceous perennial; upright and outwardly arching plant habit with flowers held above the foliar plane; shape, globular; moderately vigorous growth habit.

*Plant height.*—About 26 cm.

*Plant diameter* (*area of spread*).—About 43.7 cm.

Foliage description:

*Arrangement.*—Leaves arranged in a basal rosette; palmately compound with five leaflets per leaf.

*Leaf length.*—About 18.2 cm.

*Leaf width.*—About 22.4 cm.

*Leaflet length.*—About 13.9 cm.

*Leaflet width.*—About 4.6 cm.

*Leaf shape.*—Palmate; orbicular in outline.

*Leaflet shape.*—Elliptic to ovate.

*Leaflet apex.*—Acute.

*Leaflet base.*—Attenuate.

*Leaflet margin.*—Sharply serrate.

*Leaflet texture, upper and lower surfaces.*—Smooth, glabrous; leathery.

*Leaflet venation pattern.*—Pinnate.

*Leaflet color.*—Developing leaves, upper surface: Between N137D and 147A; base tinged with close to N186C. Developing leaves, lower surface: Close to 147B; base tinged with close to N186C. Fully developed leaves, upper surface: Close to 147A; venation, darker than between 147A and N189A. Fully developed leaves, lower surface: Close to 147B; venation, close to 147B.

*Petiole.*—Length: About 9.8 cm. Diameter: About 7 mm. Texture, upper and lower surfaces: Smooth, glabrous. Color, upper and lower surfaces: Close to 144A with spots, close to 177A.

Flower description:

*Flower shape and habit.*—Single rotate flowers; uniform flowering habit; about seven flowers per terminal cyme; flowers facing slightly outwardly to nodding.

*Fragrance.*—None detected.

*Natural flowering season.*—Long flowering period; plants flower from winter to early spring in Germany.

*Flower longevity on the plant.*—About ten days; flowers not persistent.

*Flower buds.*—Length: About 1.4 cm. Diameter: About 1 cm. Shape: Obovate. Color: Close to 144D flushed with close to 174B.

*Inflorescence height.*—About 26 cm.

*Inflorescence diameter.*—About 19.6 cm.

*Flower diameter.*—About 6.5 cm.

*Flower depth* (*height*).—About 2.6 cm.

*Petals.*—Transformed into nectaries.

*Sepals.*—Arrangement: About five in a single whorl. Length: About 3.3 cm. Width: About 2.4 cm. Shape: Broadly elliptic to broadly obovate. Apex: Rounded to emarginate. Margin: Entire. Texture, upper and lower surfaces: Smooth, glabrous. Color: When opening, upper surface: Close to 145C to 145D to 157A; towards the base, close to 145B. When opening, lower surface: Close to 145C to 145D to 157A; center flushed with close to 174C to 174D; towards the base, close to 145B. Fully opened, upper surface: Close to 145D to 157A to 157B; towards the base, close to 145B to 145C; color becoming closer to 144B with development. Fully opened, lower surface: Close to 145D to 157A to 157B; towards the base, close to 145C.

*Peduncles.*—Strength: Moderately strong. Length: About 16.7 cm. Diameter: About 1 cm. Aspect: About 10° from vertical. Texture: Smooth, glabrous. Color: Close to 145C with spots, close to 182B.

*Pedicels.*—Strength: Moderately strong. Length: About 3.6 cm. Diameter: About 3 mm. Aspect: About 30° from the peduncle axis. Texture: Smooth, glabrous. Color: Close to 145B to 145C.

*Reproductive organs.*—Stamens: Quantity per flower: About 70. Filament length: About 1.4 cm. Filament color: Close to 155C. Anther shape: Narrowly reniform. Anther length: About 2 mm. Anther color: Close to 150B. Pollen amount: Scarce. Pollen color: Close to 158D. Pistils: Quantity per flower: About six. Pistil length: About 1 cm. Stigma shape: Club-shaped. Stigma color: Close to 145C. Style length: About 9.5 mm. Style color: Close to 145C. Ovary color: Close to 145B. Nectaries (transformed petals): Quantity per flower: About 13. Length: About 9 mm. Diameter, apex: Close to 2 mm. Diameter, base: Close to 1 mm. Shape: Flattened triangular. Color: Close to N144A to N144B; towards the base, close to N144C.

*Seeds/fruits.*—Seed and fruit development have not been observed.

Garden performance: Plants of the new *Helleborus* have been observed to have good garden performance and to tolerate rain, wind and temperatures ranging from about −10° C. to about 35° C.

Pathogen/pest resistance: Plants of the new *Helleborus* have not been shown to be resistant to pathogens and pests common to *Helleborus*.

It is claimed:

1. A new and distinct *Helleborus* plant named 'COSEH 740' as illustrated and described.

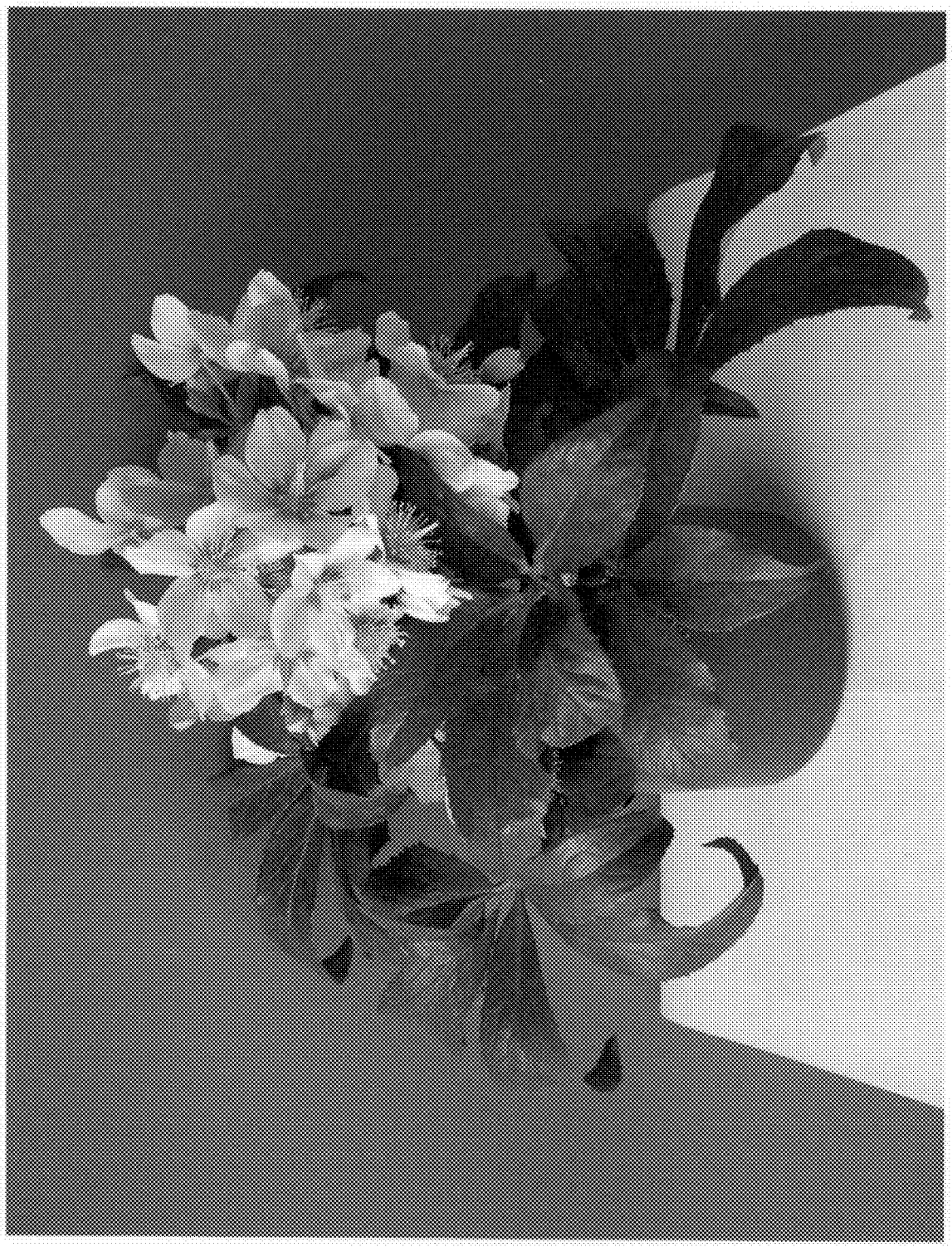

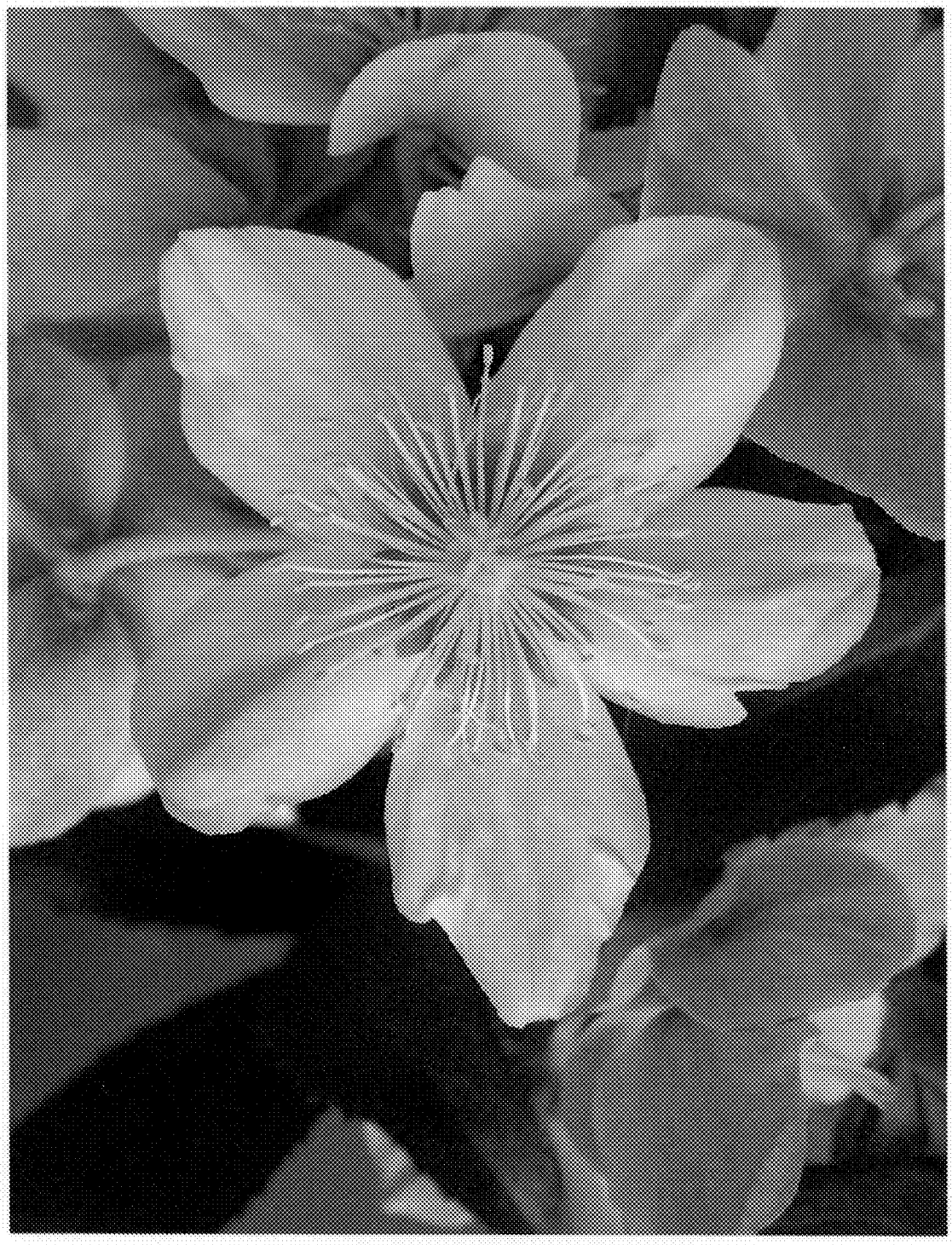

* * * * *